United States Patent [19]

Miyamoto et al.

[11] 4,169,850
[45] Oct. 2, 1979

[54] β-SULFENYL ACRYLIC ACID COMPOUNDS AND PROCESS OF PREPARING SAME

[75] Inventors: Norioki Miyamoto, Sakura; Shigeo Inoue, Saitama, both of Japan

[73] Assignee: Kao Soap Co., Ltd., Tokyo, Japan

[21] Appl. No.: 807,509

[22] Filed: Jun. 17, 1977

Related U.S. Application Data

[63] Continuation-in-part of Ser. No. 699,324, Jun. 24, 1976, abandoned.

[30] Foreign Application Priority Data

| | | | |
|---|---|---|---|
| Jul. 4, 1975 | [JP] | Japan | 50-82372 |
| Jul. 7, 1975 | [JP] | Japan | 50-83241 |
| Jul. 7, 1975 | [JP] | Japan | 50-83242 |
| Jul. 11, 1975 | [JP] | Japan | 50-84944 |
| Jul. 11, 1975 | [JP] | Japan | 50-84945 |

[51] Int. Cl.² .................. C07C 97/16; A01N 9/20; C11D 1/18
[52] U.S. Cl. .................. 260/561 S; 424/320; 252/544
[58] Field of Search .................. 260/561 S

[56] References Cited

U.S. PATENT DOCUMENTS

| | | | |
|---|---|---|---|
| 2,899,354 | 8/1959 | Kleemann et al. | 260/561 S |
| 3,228,832 | 1/1966 | Margot et al. | 260/561 S |
| 3,277,063 | 10/1966 | Harris | 260/561 S |

OTHER PUBLICATIONS

Crow "Chem. Abstract" vol. 71 (1969) p. 3313f.

*Primary Examiner*—A. Siegel
*Attorney, Agent, or Firm*—Blanchard, Flynn, Thiel, Boutell & Tanis

[57] ABSTRACT

Compounds having the formula

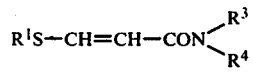

wherein $R^1$ is alkyl having 1 to 20 carbon atoms, preferably 6 to 20 carbon atoms, and $R^3$ and $R^4$ are hydrogen, alkyl having 1 to 20 carbon atoms, preferably 1 to 6 carbon atoms, or substituted alkyl having 2 to 6 carbon atoms and substituted by hydroxyl or sulfo salt. The compounds are prepared by reacting R'SH with acetylene monocarboxylic acid and then reacting the thus-formed intermediate with an amine. The compounds possess surface active and antibiotic properties.

18 Claims, No Drawings

β-SULFENYL ACRYLIC ACID COMPOUNDS AND PROCESS OF PREPARING SAME

CROSS REFERENCE TO RELATED APPLICATION

This is a continuation-in-part of U.S. patent application Ser. No. 699,324, filed June 24, 1976, now abandoned.

The present invention relates to β-sulfenyl acrylic acid amides and a method of preparing those compounds.

Many problems arise when conventional antibiotic chemicals are used. A primary problem is that each of the known antibiotic chemicals can only be applied to a small group of systems or species of micro-organisms. Under the present circumstances, it is therefore necessary to subject to various tests a number of available antibiotic chemicals in order to select a specific chemical which is suited for applying to the particular system or specie. Although the antibiotic chemicals of the phenol system have been widely used, this kind of chemical, in general, has only a narrow spectrum of antibiotic activity and it must be used at a high concentration. Antibiotic chemicals of the halogen-substituted aromatic compound system, which is a different kind of widely used antibiotic chemical, tend to be accumulated in the natural world without being decomposed, and this can cause another kind of problem. It is also known that invert soaps exhibit remarkable antibiotic activities at low concentations. However, it is difficult to apply invert soaps to a system in which it is desired to reduce lathering of the soaps or to an anionic emulsion system, because the invert soaps form insoluble complexes with such systems.

The present invention has been developed after our strenuous efforts to solve the aforementioned problems.

The present invention provides β-sulfenyl acrylic acid and derivatives thereof which have the following formula (1), and method of preparing such compounds.

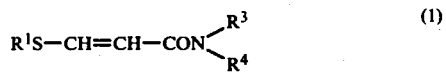

In the above formula (1), $R^1$ is alkyl having 1 to 20 carbon atoms, preferably from 6 to 20 carbon atoms and, most preferably, from 8 to 12 carbon atoms, $R^3$ and $R_4$, which can be the same or different, are hydrogen, unsubstituted alkyl having 1 to 20 carbon atoms, especially from 1 to 6 carbon atoms, or substituted alkyl having 2 to 6 carbon atoms and having a substituent selected from the group consisting of hydroxyl and a sulfo group in a form of a salt (—SO$_3$M), wherein M is an alkali metal.

β-sulfenyl acrylic acid and salts thereof having the formula (2):

wherein $R^1$ is the same as in the formula (1) and M is hydrogen or an alkali metal, are prepared by reacting mercaptans having the formula (3):

with acetylene monocarboxylic acid in an aqueous solution in the presence of an alkali metal hydroxide.

A reaction in which p-tolyl mercaptan is added to acetylene monocarboxylic acid using sodium ethoxide catalyst in ethanol is known in the art (W. E. Twce, D. L. Goldhamer & R. B. Kwse, J. Amer. Chem. Soc., vol. 81, page 4931 (1959)).

We have found that the addition reaction at the molar ratio of 1:1 between a mercaptan of the formula (3) and acetylene monocarboxylic acid takes place in an aqueous solution thereof, in the presence of a catalyst of an alkali metal hydroxide with increased yields of the desired products.

In the present invention, the mol ratio of mercaptan to acetylene monocarboxylic acid is 1:1.0 to 1.3. It is not preferred to employ an amount of acetylene monocarboxylic acid less than the above noted range, because unreacted mercaptan remains. The reaction temperature is maintained generally within the range of 0° to 100° C., preferably from 20° to 60° C. The preferred catalysts are sodium hydroxide and potassium hydroxide.

Halides of β-sulfenyl acrylic acid having the formula:

wherein $R^1$ is the same as defined above, and Y is halogen, are prepared by reacting β-sulfenyl acrylic acid with halides of inorganic acids.

Examples of halides of inorganic acids are thionyl chloride (SOCl$_2$), phosphorus trichloride (PCl$_3$), phosphorus pentachloride (PCl$_5$), phosphorus oxychloride (POCl$_3$), phosphorus tribromide (PBr$_3$) and phosphorus pentabromide (PBr$_5$).

It is preferred to employ about 1.3 to 2 mols of the inorganic acid halide per one mole of β-sulfenyl acrylic acid, in the method of the present invention.

The reaction is carried out at a reaction temperature of 0° to 70° C. generally for from 30 minutes to 4 hours. For example, a preferred reaction time period at 0° C. is 1 to 4 hours, and at 70° C. is 30 minutes to 2 hours.

A solvent may or may not be used as a reaction medium. The preferred solvents are halogenated hydrocarbon solvents such as CCl$_4$, CHCl$_3$ and CH$_2$Cl$_2$.

β-sulfenyl acrylic amides having the above formula (1) can be prepared by reacting β-sulfenyl acrylic acid or halides thereof with one or more of primary or secondary amines having the formula (4):

wherein $R^3$ and $R^4$ have the same meaning as defined above.

There are two methods for preparing such amides.

(1) A method which comprises heating to remove water from the reaction mixture which contains β-sulfenyl acrylic acid and one or more of the amines and which does not contain any solvent.

(2) A method which comprises reacting a halide of β-sulfenyl acrylic acid with one or more of the amines, in a basic solvent such as an aqueous solution of sodium hydroxide or sodium carbonate or pyridine.

In the method (1), the yield of the formed amide of the formula (1) will be increased if more than 2 mols of amines are used per 1 mol of the used acid. The generally preferred reaction temperature is 150° to 170° C., and the reaction mixture is heated until about 1 mol of water is distilled off.

In the method (2), 2 to 3 mols of amines are used per 1 mol of the used acid halide, and the reaction is allowed to proceed generally at 0° to 50° C.

Beta-sulfenyl acrylic acid per se, and derivatives thereof, according to the present invention, which are represented by the above formula (1) and the compounds represented by the formula of $R^1SO_n$—CH=CH—$CONR^3R^4$ (wherein $R^1$, $R^3$ and $R^4$ are the same as described hereinabove and n=1 or 2) which are obtainable by oxidizing the compounds of formula (1) with an organic or inorganic peroxide, have surface active properties and antibiotic functions and they can be used as detergents, germicides, disinfectants and the like.

The antibiotic activities of the individual compounds of the present invention differ from each other due to the differences in their structure, so that the compounds of the present invention with different atoms or groups as $R^1$, $R^3$ and $R^4$ have, inclusively, a wide range of antibiotic activities and are effective against a wide range of microorganisms.

β-sulfenyl acrylic amides having the formula (1) can be effectively used as dispersing agents, germicides, antifungal agents or antiseptics in cosmetic goods and mixcellaneous products for domestic use.

The present invention will be further described in more detail with reference to illustrative Examples thereof. In the Table showing the results of the antibiotic properties, there will be shown the antibiotic properties of the compounds which are obtained by oxidizing the compounds of the present invention and which are represented by the following general formula:

$$R^1SO_n\text{—CH=CH—}CONR^3R^4$$

wherein $R^1$, $R^3$ and $R^4$ are the same as in formula (1) and n=1 or 2.

EXAMPLE 1

0.50 mol of sodium hydroxide was dissolved in 500 ml of water. 0.55 mol of acetylene monocarboxylic acid was added thereto in dropwise fashion. 0.50 mol of lauryl mercaptan was then added at room temperature. After completion of the dropwise addition, the mixture was agitated at room temperature for 3 hours. The reaction mixture was neutralized with dilute hydrochloric acid and extracted with benzene to obtain a crystalline compound, the yield being 93% based on the amount of the starting mercaptan. The obtained crystalline compound was subjectd to infrared analysis (IR), nuclear magnetic resonance analysis (NMR), and elementary analysis. The results of the analyses are shown as follows:

IR:1660 (C=O) $CM^{-1}$.

NMR ($CCl_4$, TMS):δ 7.25 (doublet, 1H, =CH—COO), 5.85 ppm (doublet, 1H, —S—CH=).

Result of the elementary analysis:

|       | found | calcd. |
|-------|-------|--------|
| C (%) | 66.3  | 66.1   |
| H (%) | 10.3  | 10.4   |

From the results of the above analyses, the above crystallized compound was identified as having the following formula n—$C_{12}H_{25}$S—CH=CH—COOH The sodium salt of the above compound having the formula:

n—$C_{12}H_{25}$S—CH=CH—COONa possesses excellent surfactant activity, and the CMC (critical micelle concentration) value thereof at 50° C. was 0.60 millimol concentration.

EXAMPLE 2

Various mercaptans were reacted with acetylene monocarboxylic acid. The reaction conditions and the yields are shown in Table 1, and the properties of the reaction products are shown in Table 2.

Table 1:

| Mercaptan ($R^1SH$) $R^1$ | Preparation of β-sulfenyl acrylic acids | | | | | | Yield (% based on mercaptan) |
|---|---|---|---|---|---|---|---|
| | Quantity of acetylene monocarboxylic acid (mol) added to 0.50 mol of mercaptan | Sodium hydroxide (mol) | $H_2O$ (ml) | Reaction temp. (°C.) | Reaction period (hr) | Product | |
| $C_4H_9$ | 0.55 | 0.50 | 500 | 25 | 3 | $C_4H_9$SCH=CHCOOH | 85 |
| $C_6H_{13}$ | 0.55 | 0.50 | 500 | 25 | 3 | $C_6H_{13}$SCH=CHCOOH | 82 |
| $C_8H_{17}$ | 0.55 | 0.50 | 500 | 25 | 3 | $C_8H_{17}$SCH=CHCOOH | 88 |
| $C_{12}H_{25}$ | 0.55 | 0.50 | 500 | 25 | 3 | $C_{12}H_{25}$SCH=CHCOOH | 93 |
| $C_{14}H_{29}$ | 0.55 | 0.50 | 500 | 25 | 3 | $C_{14}H_{29}$SCH=CHCOOH | 83 |
| 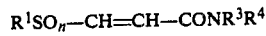 | 0.55 | 0.50 | 500 | 25 | 3 | —SCH=CHCOOH | 80 |
| $C_{18}H_{35}$ (oleyl) | 0.55 | 0.50 | 500 | 25 | 3 | $C_{18}H_{35}$SCH=CHCOOH | 83 |
| $CH_3$ | 0.55 | 0.50 | 500 | 25 | 3 | $CH_3$SCH=CHCOOH | 68 |
| $C_{20}H_{41}$ | 0.55 | 0.50 | 500 | 25 | 3 | $C_{20}H_{41}$SCH=CHCOOH | 72 |

Table 2:

| Compound | Properties of β-sulfenyl acrylic acids | | | Result of elementary analysis | | | |
|---|---|---|---|---|---|---|---|
| | Property | IR ($cm^{-1}$) | NMR ($CCl_4$, TMS, δ ppm) | found | | calcd. | |
| | | | | C (%) | H (%) | C (%) | H (%) |
| $C_4H_9$SCH=CHCOOH | mp. 88°–89° C. (in hexane) | 1663 | 7.25(doublet,1H,=CH—COO—) 5.85(doublet,1H,—S—CH=) | 52.3 | 7.5 | 52.5 | 7.6 |

Table 2:-continued

Properties of β-sulfenyl acrylic acids

| Compound | Property | IR (cm⁻¹) | NMR (CCl₄, TMS, δ ppm) | Result of elementary analysis | | | |
|---|---|---|---|---|---|---|---|
| | | | | found | | calcd. | |
| | | | | C (%) | H (%) | C (%) | H (%) |
| C₆H₁₃SCH=CHCOOH | 86°-88° C. (in hexane) | 1660 | 7.21(doublet,1H,=CH—COO—) 5.83(doublet,1H,—S—CH=) | 57.1 | 8.3 | 57.4 | 8.6 |
| C₈H₁₇SCH=CHCOOH | 90°-93° C. (in hexane) | 1658 | 7.20(doublet,1H,=CH—COO—) 5.65(doublet,1H,—S—CH=) | 60.7 | 9.1 | 61.1 | 9.3 |
| C₁₂H₂₅SCH=CHCOOH | 92°-94° C. (in hexane) | 1660 | 7.24(doublet,1H,=CH—COO—) 5.80(doublet,1H,—S—CH=) | 66.3 | 10.3 | 66.1 | 10.4 |
| C₁₄H₂₉SCH=CHCOOH | 93°-95° C. (in hexane) | 1660 | 7.18(doublet,1H,=CH—COO—) 5.79(doublet,1H,—S—CH=) | 67.8 | 10.9 | 68.0 | 10.7 |
| ⌬—SCH=CHCOOH | 110°-112° C. (in hexane) | 1663 | 7.26(doublet,1H,=CH—COO—) 5.76(doublet,1H,—S—CH=) | 60.3 | 4.4 | 60.0 | 4.5 |
| C₁₈H₃₅SCH=CHCOOH | 56°-57° C. (in hexane) | 1670 | 7.26(doublet,1H,=CH=COO—) 5.60(doublet,1H,—S—CH=) | 69.9 | 10.6 | 71.1 | 10.8 |
| CH₃SCH=CHCOOH | liquid | 1660 | 7.30(doublet,1H,=CH—COO—) 5.60(doublet,1H,—S—CH=) | 40.5 | 5.0 | 40.7 | 5.1 |
| C₂₀H₄₁SCH=CHCOOH | 89°-90° C. | 1665 | 7.38(doublet,1H,=CH—COO—) 5.21(doublet,1H,—S—CH=) | 71.4 | 11.6 | 71.8 | 11.5 |

EXAMPLE 3

0.30 mol of β-lauryl sulfenyl acrylic acid synthesized in Example 1 was dissolved in 200 ml of CCl₄. 0.45 mol of SOCl₂ was added to the obtained solution dropwise at room temperature and the solution was agitated at room temperature for 1 hour. CCl₄ and excess SOCl₂ were then removed under reduced pressure, and a viscous liquid was obtained at a yield of 92%. The results of the analyses of the liquid were as follows:

IR:1775 (C=O) cm⁻¹.
NMR (CCl₄, TMS):δ 7.20 (doublet, 1H, =CH—COCl) 5.78 ppm (doublet, 1H, —S—CH=)
Result of the elementary analysis:

| | found | calcd. |
|---|---|---|
| C (%) | 61.7 | 61.9 |
| H (%) | 9.6 | 9.4 |

From the results of the above analyses, the above viscous liquid was identified as having the formula:

n—C₁₂H₂₅S—CH=CH—COCl

EXAMPLE 4

Various halides of β-sulfenyl acrylic acid were synthesized. The reaction conditions and the yields are shown in Table 3.

Table 3:

Preparation of halides of β-sulfenyl acrylic acid

| Used β-sulfenyl acrylic acid R¹ | Used halogenation agent | Quantity of halogenating agent (mol) added to 0.30 mol of β-sulfenyl acrylic acid | Solvent | Reaction temp. (°C.) | Reaction period (hr) | Product | State | Yield based on β-sulfenyl acrylic acid (%) |
|---|---|---|---|---|---|---|---|---|
| C₁₂H₂₅ | SOCl₂ | 0.45 | (CCl₄(200ml)) | 25 | 1.0 | C₁₂H₂₅SCH=CH—COCl | liquid | 92 |
| | | 0.39 | | 70 | 1.0 | | | 68 |
| | PCl₃ | 0.45 | (CCl₄(200ml)) | 25 | 1.5 | | | 76 |
| | | 0.39 | | 70 | 1.5 | | | 62 |
| | PCl₅ | 0.45 | (CCl₄(200ml)) | 25 | 1.3 | | | 83 |
| | | 0.39 | | 70 | 1.3 | | | 55 |
| | POCl₃ | 0.45 | (CCl₄(200ml)) | 25 | 2.0 | | | 64 |
| | | 0.39 | | 70 | 2.0 | | | 55 |
| | PBr₃ | 0.45 | (CCl₄(200ml)) | 25 | 1.3 | C₁₂H₂₅SCH=CH—COBr | liquid | 83 |
| | | 0.39 | | 70 | 1.3 | | | 70 |
| | PBr₅ | 0.45 | (CCl₄(200ml)) | 25 | 1.3 | | | 68 |
| | | 0.39 | | 70 | 1.3 | | | 62 |

Table 3:-continued
Preparation of halides of β-sulfenyl acrylic acid

| Used β-sulfenyl acrylic acid R¹ | Used halogenation agent | Quantity of halogenating agent (mol) added to 0.30 mol of β-sulfenyl acrylic acid | Solvent | Reaction temp. (°C.) | Reaction period (hr) | Product | State | Yield based on β-sulfenyl acrylic acid (%) |
|---|---|---|---|---|---|---|---|---|
| Phenyl | SOCl₂ | 0.45 / 0.39 | (CCl₄(200ml)) | 25 / 70 | 1.0 / 1.0 | PhSCH=CH—COCl | liquid | 80 / 62 |
|  | PCl₃ | 0.45 / 0.39 | (CCl₄(200ml)) | 25 / 70 | 1.5 / 1.5 |  |  | 74 / 72 |
|  | PCl₅ | 0.45 / 0.39 | (CCl₄(200ml)) | 25 / 70 | 1.3 / 1.3 |  |  | 63 / 60 |
|  | POCl₃ | 0.45 / 0.39 | (CCl₄(200ml)) | 25 / 70 | 2.0 / 2.0 |  |  | 74 / 68 |
| Phenyl | PBr₃ | 0.45 / 0.39 | (CCl₄(200ml)) | 25 / 70 | 1.3 / 1.3 | PhSCH=CH=COBr | liquid | 80 / 72 |
|  | PBr₅ | 0.45 / 0.39 | (CCl₄(200ml)) | 25 / 70 | 1.3 / 1.3 |  |  | 64 / 55 |
| CH₃ | SOCl₂ | 0.45 / 0.39 | (CCl₄(200ml)) | 25 / 70 | 1.0 / 1.0 | CH₃SCH=CHCOCl | liquid | 88 / 60 |
|  | PCl₃ | 0.45 / 0.39 | (CCl₄(200ml)) | 25 / 70 | 1.5 / 1.5 |  |  | 70 / 58 |
|  | PCl₅ | 0.45 / 0.39 | (CCl₄(200ml)) | 25 / 70 | 1.3 / 1.3 |  |  | 63 / 60 |
|  | POCl₃ | 0.45 / 0.39 | (CCl₄(200ml)) | 25 / 70 | 2.0 / 2.0 |  |  | 80 / 61 |
|  | PBr₃ | 0.45 / 0.39 | (CCl₄(200ml)) | 25 / 70 | 1.3 / 1.3 | CH₃SCH=CHCOBr | liquid | 75 / 60 |
|  | PBr₅ | 0.45 / 0.39 | (CCl₄(200ml)) | 25 / 70 | 1.3 / 1.3 |  |  | 68 / 55 |
| C₂₀H₄₁ | SOCl₂ | 0.45 / 0.39 | (CCl₄(200ml)) | 25 / 70 | 1.0 / 1.0 |  |  | 75 / 55 |
|  | PCl₃ | 0.45 / 0.39 | (CCl₄(200ml)) | 25 / 70 | 1.5 / 1.5 | C₂₀H₄₁SCH=CHCOCl | liquid | 68 / 48 |
| C₂₀H₄₁ | PCl₅ | 0.45 / 0.39 | (CCl₄(200ml)) | 25 / 70 | 1.3 / 1.3 |  |  | 75 / 62 |
|  | POCl₃ | 0.45 / 0.39 | (CCl₄(200ml)) | 25 / 70 | 2.0 / 2.0 |  |  | 66 / 48 |
|  | PBr₃ | 0.45 / 0.39 | (CCl₄(200ml)) | 25 / 70 | 1.3 / 1.3 | C₂₀H₄₁SCH=CHCOBr | liquid | 55 / 38 |
|  | PBr₅ | 0.45 / 0.39 | (CCl₄(200ml)) | 25 / 70 | 1.3 / 1.3 |  |  | 64 / 32 |
| Oleyl | SOCl₂ | 0.45 | (CCl₄(200ml)) | 25 | 1.0 |  |  | 80 |

Table 3:-continued
Preparation of halides of β-sulfenyl acrylic acid

| Used β-sulfenyl acrylic acid R¹ | Used halogenation agent | Quantity of halogenating agent (mol) added to 0.30 mol of β-sulfenyl acrylic acid | Solvent | Reaction temp. (°C.) | Reaction period (hr) | Product | State | Yield based on β-sulfenyl acrylic acid (%) |
|---|---|---|---|---|---|---|---|---|
| ($C_{18}H_{35}$) |  | 0.39 |  | 70 | 1.0 |  |  | 61 |
|  | $PCl_3$ | 0.45 | ($CCl_4$(200ml)) | 25 | 1.5 |  |  | 63 |
|  |  | 0.39 |  | 70 | 1.5 | $C_{18}H_{35}SCH=CHCOCl$ | liquid | 33 |
|  | $PCl_5$ | 0.45 | ($CCl_4$(200ml)) | 25 | 1.3 |  |  | 75 |
|  |  | 0.39 |  | 70 | 1.3 |  |  | 60 |
|  | $POCl_3$ | 0.45 | ($CCl_4$(200ml)) | 25 | 2.0 |  |  | 63 |
|  |  | 0.39 |  | 70 | 2.0 |  |  | 33 |
|  | $PBr_3$ | 0.45 | ($CCl_4$(200ml)) | 25 | 1.3 |  |  | 81 |
|  |  | 0.39 |  | 70 | 1.3 | $C_{18}H_{35}SCH=CHCOBr$ | liquid | 70 |
|  | $PBr_5$ | 0.45 | ($CCl_4$(200ml)) | 25 | 1.3 |  |  | 63 |
|  |  | 0.30 |  | 70 | 1.3 |  |  | 60 |

EXAMPLE 5

0.3 mol of β-lauryl sulfenyl acrylic acid synthesized in Example 1 and 0.75 mol of diethanol amine were heated at 170° C. for 3 hours, and the formed water was distilled off. The reaction mixture was then poured into 300 ml of water, and extracted with diethyl ether to obtain a viscous liquid at a yield of 65%.

The results of the analyses of the obtained liquid are set forth below.

IR: (1630 (cm$^{-1}$).
NMR ($CCl_4$, TMS): δ 7.30 (doublet, 1H, =CH—CON), 5.90 ppm (doublet, 1H, —S—CH=)
Result of the elementary analysis:

|  | found | calcd. |
|---|---|---|
| C (%) | 63.3 | 63.5 |
| H (%) | 10.3 | 10.4 |

From the results of the above analyses, the above liquid was identified as having the formula:

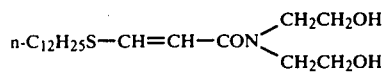

$$\text{n-}C_{12}H_{25}S\text{—}CH=CH\text{—}CON\diagup^{CH_2CH_2OH}_{CH_2CH_2OH}$$

EXAMPLE 6

1.5 mols of dimethyl amine was dissolved in 100 ml of pyridine. 0.30 mol of chloride of β-lauryl sulfenyl acrylic acid synthesized in Example 3 was added in drops to the solution. The reaction mixture was agitated at 25° C. for 1 hour. The reaction mixture was then poured into 200 ml of water and extracted with diethyl ether to obtain a liquid at a yield of 82%.

The results of the analyses of the above liquid are set forth below.

IR: 1635 (cm$^{-1}$).
NMR ($CCl_4$, TMS): δ 7.25 (doublet, 1H, =CH—CON—), 5.93 ppm (doublet, 1H, —S—CH=)
Result of the elementary analysis:

|  | found | calcd. |
|---|---|---|
| C (%) | 68.4 | 68.1 |
| H (%) | 10.9 | 11.1 |

From the results of the above analyses, the above liquid was identified as having the formula:

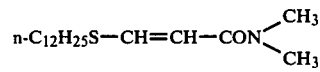

$$\text{n-}C_{12}H_{25}S\text{—}CH=CH\text{—}CON\diagup^{CH_3}_{CH_3}$$

EXAMPLE 7

0.6 mol of taurine ($NH_2CH_2CH_2OSO_2Na$) and 0.6 mol of $Na_2CO_3$ were dissolved in 200 ml of water. 0.3 mol of β-lauryl sulfenyl acrylic chloride synthesized in Example 3 was added to the solution and reacted at 25° C. for 1 hour. Water was removed from the reaction mixture. The fraction which is soluble in isopropyl alcohol was then concentrated to obtain a crystallized compound. The results of the analyses of the crystallized compound are set forth below.

IR: 1630 (cm$^{-1}$).
NMR ($CD_3OD$), TMS): δ 7.20 (doublet, 1H, =CH—CON—), 5.91 ppm (doublet, 1H, —S—CH=)
Result of the elementary analysis:

|  | found | calcd. |
|---|---|---|
| C (%) | 50.5 | 50.8 |
| H (%) | 7.8 | 8.0 |

From the results of the above analyses, the above crystallized compound was identified as having the formula:

n—$C_{12}H_{25}$S—CH=CH—CONHCH$_2$CH$_2$SO$_3$Na

EXAMPLE 8

Various β-sulfenyl acrylic amides were prepared. The reaction conditions and the yields are shown in Table 4, and the properties of the formed substances are shown in Table 5.

Table 4:
Preparation of β-sulfenyl acrylic amides

| Used compound (4) R¹ | Y: | Used amine R³R⁴NH: | Quantity of (R³R⁴NH) (mol) added to 0.30 mol of the used compound (4) | Solvent | Reaction temp. (°C.) | Reaction period (hr) | Product | Yield based the used compound (4) (%) |
|---|---|---|---|---|---|---|---|---|
| $C_{12}H_{25}$ | Cl | $R^3=CH_3$, $R^4=CH_3$ | 1.5 | pyridine (100ml) | 25 | 1 | $C_{12}H_{25}SCH=CHCON(CH_3)(CH_3)$ | 82 |
| $C_{12}H_{25}$ | OH | $R^3=CH_2CH_2OH$, $R^4=CH_2CH_2OH$ | 1.5 | — | 170 | 3 | $C_{12}H_{25}SCH=CHCON(CH_2CH_2OH)(CH_2CH_2OH)$ | 65 |
| $C_{12}H_{25}$ | Cl | $R^3=H$, $R^4=CH_2CH_2SO_3Na$ | 0.6 | $Na_2CO_3$(0.6mol) $H_2O$(200ml) | 50 | 1 | $C_{12}H_{25}S-CH=CH-CONHCH_2CH_2SO_3Na$ | 72 |
| Ph | Cl | $R^3=CH_3$, $R^4=CH_3$ | 1.5 | pyridine (100ml) | 25 | 1 | $PhSCH=CHCON(CH_3)(CH_3)$ | 68 |
| Ph | OH | $R^3=CH_2CH_2OH$, $R^4=CH_2CH_2OH$ | 1.5 | — | 170 | 3 | $PhSCH=CHCON(CH_2CH_2OH)(CH_2CH_2OH)$ | 65 |
| Ph | Cl | $R^3=H$, $R^4=CH_2CH_2SO_3Na$ | 0.6 | $Na_2CO_3$(0.6mol) $H_2O$(200ml) | 50 | 1 | $PhSCH=CHCONHCH_2CH_2SO_3Na$ | 53 |
| $CH_3$ | Cl | $R^3=CH_3$, $R^4=CH_3$ | 1.5 | pyridine (100ml) | 25 | 1 | $CH_3SCH=CHCON(CH_3)(CH_3)$ | 63 |
| $CH_3$ | OH | $R^3=CH_2CH_2OH$, $R^4=CH_2CH_2OH$ | 1.5 | — | 170 | 3 | $CH_3SCH=CHCON(CH_2CH_2OH)(CH_2CH_2OH)$ | 55 |
| $CH_3$ | Cl | $R^3=H$, $R^4=CH_2CH_2SO_3Na$ | 0.6 | $Na_2CO_3$(0.6mol) $H_2O$(200ml) | 50 | 1 | $CH_3SCH=CHCONHCH_2CH_2SO_3Na$ | 72 |
| $C_{20}H_{41}$ | Cl | $R^3=CH_3$, $R^4=CH_3$ | 1.5 | pyridine (100ml) | 27 | 1 | $C_{20}H_{41}SCH=CHCON(CH_3)(CH_3)$ | 64 |
| $C_{20}H_{41}$ | OH | $R^3=CH_2CH_2OH$, $R^4=CH_2CH_2OH$ | 1.5 | — | 170 | 3 | $C_{20}H_{41}SCH=CHCON(CH_2CH_2OH)(CH_2CH_2OH)$ | 53 |
| $C_{20}H_{41}$ | Cl | $R^3=H$, $R^4=CH_2CH_2SO_3Na$ | 0.6 | $Na_2CO_3$(0.6mol) $H_2O$(200ml) | 50 | 1 | $C_{20}H_{41}SCH=CHCONHCH_2CH_2SO_3Na$ | 70 |

Table 4-continued

Preparation of β-sulfenyl acrylic amides

| Used compound (4) R¹: | Y: | Used amine R³R⁴NH: | Quantity of (R³R⁴NH) (mol) added to 0.30 mol of the used compound (4) | Solvent | Reaction temp. (°C) | Reaction period (hr) | Product | Yield based the used compound (4) (%) |
|---|---|---|---|---|---|---|---|---|
| Oleyl ($C_{18}H_{35}$) | Cl | $R^3 = CH_3$<br>$R^4 = CH_3$ | 1.5 | pyridine (100ml) | 25 | 1 | $C_{18}H_{35}SCH=CHCON\begin{smallmatrix}CH_3\\CH_3\end{smallmatrix}$ | 83 |
| | OH | $R^3 = CH_2CH_2OH$<br>$R^4 = CH_2CH_2OH$ | 1.5 | — | 170 | 3 | $C_{18}H_{33}SCH=CHCON\begin{smallmatrix}CH_2CH_2OH\\CH_2CH_2OH\end{smallmatrix}$ | 76 |
| | Cl | $R^3 = H$<br>$R^4 = CH_2CH_2SO_3Na$ | 0.6 | $Na_2CO_3$(0.6mol) $H_2O$(200ml) | 50 | 1 | $C_{18}H_{35}SCH=CHCONHCH_2CH_2SO_3Na$ | 63 |

Table 5

Properties of β-sulfenyl acrylic amides

| Compound | Property | IR(cm$^{-1}$) | NMR(CCl$_4$TMS,δ,ppm) | Results of elementary analysis | | | |
|---|---|---|---|---|---|---|---|
| | | | | found | | calcd. | |
| | | | | C(%) | H(%) | C(%) | H(%) |
| C$_{12}$H$_{25}$SCH=CHCON⟨CH$_3$, CH$_3$⟩ | liquid | 1635 (—CON—) | 7.25(doublet,1H,=CH—CON—) 5.93(doublet,1H,—S—CH=) | 68.4 | 10.9 | 68.1 | 11.1 |
| C$_{12}$H$_{25}$SCH=CHCON⟨CH$_2$CH$_2$OH, CH$_2$CH$_2$OH⟩ | liquid | 1630 (—CON—) | 7.30(doublet,1H,=CH—CON—) 5.90(doublet,1H,—S—CH=) | 63.3 | 10.3 | 63.5 | 10.4 |
| C$_{12}$H$_{25}$SCH=CHCONHCH$_2$CH$_2$SO$_3$Na | m.p. 110°–115° C. (from isopropyl alcohol) | 1630 (—CON—) | 7.20(doublet,1H,=CH—CON—) 5.91(doublet,1H,—S—CH=) [CD$_3$OD,TMS] | 50.5 | 7.8 | 50.8 | 8.0 |
| PhSCH=CHCON⟨CH$_3$, CH$_3$⟩ | liquid | 1632 (—CON—) | 7.30(doublet,1H,=CH—CON—) 5.89(doublet,1H,—S—CH=) | 63.7 | 6.1 | 63.8 | 6.3 |
| PhSCH=CHCON⟨CH$_2$CH$_2$OH, CH$_2$CH$_2$OH⟩ | liquid | 1630 (—CON—) | 7.26(doublet,1H,=CH—CON—) 5.91(doublet,1H,—S—CH=) | 58.7 | 6.3 | 58.4 | 6.4 |
| PhSCH=CHCONCH$_2$CH$_2$SO$_3$Na | m.p. 120°–123° C. from isopropyl alcohol | 1628 (—CON—) | 7.24(doublet,1H,=CH—CON—) 5.92(doublet,1H,—S—CH=) [CD$_3$OD, TMS] | 42.5 | 4.3 | 42.7 | 3.9 |
| CH$_3$SCH=XHCON⟨CH$_3$, CH$_3$⟩ | liquid | 1630 (—CON—) | 7.20(doublet,=CH—CON—) 5.86(doublet,—S—CH=) | 49.3 | 7.4 | 49.6 | 7.6 |
| CH$_3$SCH=CHCON⟨CH$_2$CH$_2$OH, CH$_2$CH$_2$OH⟩ | liquid | 1628 (—CON—) | 7.23(doublet,=CH—CON—) 5.92(doublet,—S—CH—) | 46.9 | 47.4 | 46.8 | 7.4 |
| CH$_3$SCH=CHCONHCH$_2$CH$_2$SO$_3$Na | m.p. 120°–121° C. (from isopropyl alcohol) | 1629 (—CON—) | 7.18(doublet,=CH—CON—) 5.95 doublet,—S—CH=) [inCD$_3$OD] | 29.3 | 4.1 | 29.1 | 4.0 |
| C$_{20}$H$_{41}$SCH=CHCON⟨CH$_3$, CH$_3$⟩ | liquid | 1631 (—CON—) | 7.26(doublet,=CH—CON—) 5.73(doublet,—S—CH=) | 72.6 | 11.8 | 72.9 | 12.0 |

Table 5-continued

Properties of β-sulfenyl acrylic amides

| Compound | Property | IR(cm$^{-1}$) | NMR(CCl$_4$TMS,δ,ppm) | found C(%) | found H(%) | calcd. C(%) | calcd. H(%) |
|---|---|---|---|---|---|---|---|
| C$_{20}$H$_{41}$SCH=CHCON(CH$_2$CH$_2$OH)(CH$_2$CH$_2$OH) | liquid | 1630 (—CON—) | 7.19(doublet,=CH—CON—) 5.84(doublet,—S—CH=) | 68.5 | 11.3 | 68.7 | 11.3 |
| C$_{20}$H$_{41}$SCH=CHCONHCH$_2$CH$_2$SO$_3$Na | m.p. 130°–131° C. (from isopropyl alcohol) | 1630 (—CON—) | 7.62(doublet,=CH—CON—) 5.33(doublet,—S—CH=) [inCD$_3$OD] | 59.3 | 9.2 | 59.4 | 9.1 |
| C$_{18}$H$_{35}$SCH=CHCON(CH$_3$)(CH$_3$) | liquid | 1630 (—CON—) | 7.82(doublet,=CH—CON—) 5.34(doublet,—S—CH=) | 74.2 | 8.8 | 74.4 | 9.0 |
| C$_{18}$H$_{35}$SCH=CHCON(CH$_2$CH$_2$OH)(CH$_2$CH$_2$OH) | liquid | 1628 (—CON—) | 7.53(doublet,=CH—CON—) 5.76(doublet,—S—CH=) | 73.5 | 11.4 | 73.3 | 11.6 |
| C$_{18}$H$_{35}$SCH=CHCONHCH$_2$CH$_2$SO$_3$Na | m.p. 120°–121° C. from isopropyl alcohol | 1630 —CON— | 7.24(doublet,=CH—CON—) 5.86(doublet,—S—CH=) [inCD$_3$OD] | 57.4 | 8.6 | 57.1 | 8.7 |

EXAMPLE 9

This Example shows the list of compounds having antibiotic activities and the growth preventing effects thereof against the organisms positive to and negative to Gram's staining.

In accordance with the test method using agar culture media mixed with the compounds, the concentrations of compounds necessary for preventing growth of various organisms were determined.

1 ml of a solution of each of the compounds having predetermined concentration as set forth in the following Tables 6 and 7 was put on a Petri dish, and 19 ml of Sabouraud's agar culture medium preliminarily heated to be a molten state was then added to and uniformly mixed with the above solution, and the mixture was allowed to cool and solidify. One platinum loop of an organism solution containing one million cells of organism per 1 ml was coated on the surface of the solidified culture medium, and cultivated for 72 hours in a thermostatic chamber maintained at 30° C. The state of growth of the organism on each culture medium after cultivation was observed, and the minimum concentration of the respective compounds necessary to be contained in each of the culture medium was determined.

Table 6

| Compound | Staphylocuccus aureas 1000 | 500 | 100 | Bacillus subtilis 1000 | 500 | 100 |
|---|---|---|---|---|---|---|
| $n\text{-}C_4H_9\text{--}S\text{--}CH\text{=}CHCON(CH_2CH_2OH)_2$ | − | ± | + | − | + | + |
| $n\text{-}C_4H_9\overset{O}{\underset{\|}{\text{--}S\text{--}}}CH\text{=}CHCON(CH_2CH_2OH)_2$ | − | − | − | − | − | ± |
| $n\text{-}C_4H_9\overset{O}{\underset{\|}{\text{--}S\text{--}}}CH\text{=}CHCON(CH_2CH_2OH)_2$ | | − | − | + | − | − | + |
| $n\text{-}C_7H_{15}CON(CH_2CH_2OH)_2$ (Reference) | − | + | + | − | + | + |
| $HO\text{--}\bigcirc\text{--}CO_2C_2H_5$ (Reference) | − | − | + | − | ± | + |

(Note)
+ : Growth was observed; Growth preventing effect was not found.
± : Growth was observed to some extent; Growth preventing effect was found to an appreciable extent.
− : Growth was not observed; Perfect growth preventing effect is found.

Table 7

| Compounds | Staphylococcus aureus 1000 | 500 | 100 | Bacillus subtilis 1000 | 500 | 100 | Escherichia coli 1000 | 500 | 100 | Proteus vulgaris 1000 | 500 | 100 | Pseudomona aeruginosa 1000 | 500 | 100 |
|---|---|---|---|---|---|---|---|---|---|---|---|---|---|---|---|
| n-$C_4H_9$—S—CH=CH—CON($CH_2CH_2OH$)$_2$ | − | − | − | − | − | − | − | ± | + | − | − | + | − | + | + |
| n-$C_5H_{13}$—S—CH=CHCON($CH_2CH_2OH$)$_2$ | − | − | − | − | − | ± | − | + | + | − | + | + | + | + | + |
| n-$C_8H_{17}$—S—CH=CHCON($CH_2CH_2OH$)$_2$ | − | − | − | − | − | + | − | + | + | ± | + | + | + | + | + |
| n-$C_{10}H_{21}$—S—CH=CH—CON($CH_2CH_2OH$)$_2$ | − | − | − | − | + | + | ± | + | + | − | + | + | + | + | + |
| n-$C_{12}H_{25}$—S—CH=CHCON($CH_2CH_2OH$)$_2$ | − | − | + | − | − | + | + | + | + | + | + | + | + | + | + |
| n-$C_{14}H_{20}$—S—CHCON($CH_2CH_2OH$)$_2$ | + | + | + | + | + | + | + | + | + | + | + | + | + | + | + |
| n-$C_{10}H_{32}$—S—CHCON($CH_2CH_2OH$)$_2$ | − | − | − | − | − | + | − | + | + | − | + | + | + | + | + |
| n-$C_4H_9$—S—CH=CH—CONH$_2$ | − | − | + | − | − | + | − | + | + | − | + | ± | ± | + | + |
| n-$C_4H_9$—S—CH=CH—CONH$_2$ | − | − | − | − | − | − | − | ± | + | − | + | + | + | + | + |
| n-$C_4H_9$—S—CH=CH—CONH$_2$ | − | − | − | − | ± | + | − | + | + | − | + | + | + | + | + |
| n-$C_4H_9$—S—CH=CH—CON(CH$_3$)(CH$_3$) | + | + | + | + | + | + | + | + | + | ± | ± | ± | − | + | + |
| n-$C_8H_{17}$—S—CH=CH—CON($CH_2CH_2OH$)$_2$ | + | + | + | + | + | + | + | + | + | + | + | + | + | + | + |
| n-$C_4H_9$—S—CH=CH—CONHCH$_2$CH$_2$SO$_3$Na | + | + | + | + | + | + | + | + | + | + | + | + | + | + | + |
| n-$C_{11}H_{23}$CON($CH_2CH_2OH$)$_2$ (Reference) | − | + | + | − | + | + | + | + | + | + | + | + | + | + | + |
| COONa / OH (Reference) | − | + | + | − | + | + | ± | + | + | ± | + | + | + | + | + |

Table 7-continued
Minimum Conc. for Preventing Growth
| Compounds | Staphylococcus aureus | | | Bacillus subtilis | | | Escherichia coli | | | Proteus vulgaris | | | Pseudomona aeruginosa | | |
|---|---|---|---|---|---|---|---|---|---|---|---|---|---|---|---|
| | 1000 | 500 | 100 | 1000 | 500 | 100 | 1000 | 500 | 100 | 1000 | 500 | 100 | 1000 | 500 | 100 |
| 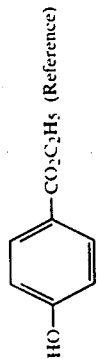—CO₂C₂H₅ (Reference) | − | − | + | − | ± | + | − | ± | + | − | − | + | ± | + | + |

EXAMPLE 10

(Fungicidal Activity Test to *Helminthosporium Oryzae*)

In synthetic resin pots having a length of 16 cm, a width of 10 cm and a depth of 5 cm, there were placed twenty rice stubbles which had been cultivated in a hothouse until they grew to the four leaves stage. Then twenty ml of an aqueous solution containing 500 ppm of a test compound was sprayed onto the rice plants in each of the pots. A control sample of rice stubble was not treated with any test compound. The rice plants were allowed to stand for one day in the hothouse after the spraying. Then an aqueous dispersion of the fruit bodies of *Helminthosporium Oryzae* virus was sprayed and inoculated uniformly onto the rice plants. The fruit bodies had been obtained by culturing in a test tube. Then, each pot having the inoculated rice plants was placed into a thermostat tank maintained at 27° C. and a relative humidity of 95 or more percent in order that the rice plants might be infected. Five days after the plants were infected with the virus, the affected spots on each leaf were observed and the fungicidal activity was calculated in comparison with the observation of affected areas of the control sample on which the test compound had not been sprayed. The fungicidal activity was calculated from the following formula:

$$\text{fungicidal activity} = \left(1 - \frac{Y}{X}\right) \times 100$$

in which Y is the number of affected spots per one treated leaf and X is the number of affected spots per one control leaf. The results are shown in Table 8. The test compounds did not otherwise have a bad effect on the growth of the plants.

Table 8

| Compound | Concentration of Test Compound (ppm) | Fungicidal activity (%) |
|---|---|---|
| $CH_3SCH=CHCONH_2$ | 500 | 53 |
| $CH_3SCH=CHCON(CH_3)_2$ | 500 | 48 |
| $CH_3SOCH=CHCON(CH_3)_2$ | 500 | 47 |
| $CH_3SO_2CH=CHCON(CH_3)_2$ | 500 | 50 |
| $C_2H_5SCH=CHCONH_2$ | 500 | 62 |
| $C_2H_5SOCH=CHCON(CH_3)_2$ | 500 | 60 |

Table 8-continued

| Compound | Concentration of Test Compound (ppm) | Fungicidal activity (%) |
|---|---|---|
| $n\text{-}C_4H_9SCH=CHCONH_2$ | 500 | 64 |
| $n\text{-}C_4H_9SCH=CHCON(CH_3)_2$ | 500 | 58 |
| $n\text{-}C_4H_9SOCH=CHCON(CH_3)_2$ | 500 | 62 |
| $n\text{-}C_4H_9SO_2CH=CHCON(CH_3)_2$ | 500 | 65 |
| $n\text{-}C_6H_{13}SCH=CHCONH_2$ | 500 | 63 |
| $n\text{-}C_6H_{13}SOCH=CHCON(CH_3)_2$ | 500 | 67 |
| $n\text{-}C_6H_{13}SO_2CH=CHCONH_2$ | 500 | 57 |
| $n\text{-}C_8H_{17}SCH=CHCONH_2$ | 500 | 73 |
| $n\text{-}C_8H_{17}SCH=CHCON(CH_3)_2$ | 500 | 82 |
| $n\text{-}C_8H_{17}SOCH=CHCON(n\text{-}CH_2CH_2CH_3)(H)$ | 500 | 76 |
| $n\text{-}C_{10}H_{21}SCH=CHCON(CH_3)_2$ | 500 | 90 |
| $n\text{-}C_{10}H_{21}SO_2CH=CHCON(CH_2CH_2OH)_2$ | 500 | 81 |
| $n\text{-}C_{12}H_{25}SCH=CHCON(CH_3)_2$ | 500 | 88 |
| $n\text{-}C_{12}H_{25}SCH=CHCON(n\text{-}CH_2CH_2CH_3)(H)$ | 500 | 95 |
| $n\text{-}C_{12}H_{25}SOCH=CHCONHCH_2CH_2SO_3Na$ | 500 | 91 |
| $n\text{-}C_{12}H_{25}SO_2CH=CHCON(CH_3)_2$ | 500 | 92 |
| $n\text{-}C_{12}H_{25}SCH=CHCONHCH_2CH_2COONa$ | 500 | 87 |

EXAMPLE 11

(Fungicial Activity Test to *Colletorichum Lagenarium*)

Twenty ml of a liquid agent containing 500 ppm of a test compound was sprayed on a cucumber plant planted in a pot. On the next day, a liquid dispersion of fruit bodies of *Colletorichum Lagenarium* was sprayed with a microsprayer and inoculated on the cucumber in an inoculating box maintained at 27° C. and a relative humidity of 95 or more percent. Two days after the inoculation, each pot was placed in a hothouse and seven days thereafter the affected spots that had appeared on the leaf were observed. The fungicidal activity was calculated in the same manner as in Example 10. The results are shown in Table 9.

Table 9

| Test Compound | Concentration of Test Compound (ppm) | Fungicidal activity (%) |
|---|---|---|
| $CH_3SCH=CHCONH_2$ | 500 | 49 |
| $CH_3SCH=CHCON(CH_3)_2$ | 500 | 53 |
| $CH_3SOCH=CHCON(CH_3)_2$ | 500 | 55 |
| $C_2H_5SCH=CHCONH_2$ | 500 | 60 |

Table 9-continued

| Test Compound | Concentration of Test Compound (ppm) | Fungicidal activity (%) |
|---|---|---|
| $C_2H_5SOCH=CHCON\begin{smallmatrix}CH_3\\CH_3\end{smallmatrix}$ | 500 | 63 |
| $n\text{-}C_4H_9SOCH=CHCON\begin{smallmatrix}CH_3\\CH_3\end{smallmatrix}$ | 500 | 70 |
| $n\text{-}C_4H_9SO_2CH=CHCONH_2$ | 500 | 72 |
| $n\text{-}C_4H_9SCH=CHCON\begin{smallmatrix}CH_3\\CH_3\end{smallmatrix}$ | 500 | 75 |
| $n\text{-}C_8H_{17}SCH=CHCON\begin{smallmatrix}n\text{-}CH_2CH_2CH_3\\H\end{smallmatrix}$ | 500 | 82 |
| $n\text{-}C_8H_{17}SOCH=CHCON\begin{smallmatrix}n\text{-}CH_2CH_2CH_3\\H\end{smallmatrix}$ | 500 | 80 |
| $n\text{-}C_8H_{17}SO_2CH=CHCON\begin{smallmatrix}n\text{-}CH_2CH_2CH_3\\H\end{smallmatrix}$ | 500 | 85 |
| $n\text{-}C_8H_{17}SOCH=CHCON(CH_2CH_2OH)_2$ | 500 | 79 |
| $n\text{-}C_{10}H_{21}SCH=CHCON\begin{smallmatrix}CH_3\\CH_3\end{smallmatrix}$ | 500 | 92 |
| $n\text{-}C_{10}H_{21}SCH=CHCONHCH_2CH_2SO_3Na$ | 500 | 87 |
| $n\text{-}C_{12}H_{25}SCH=CHCONH_2$ | 500 | 100 |
| $n\text{-}C_{12}H_{25}SCH=CHCON\begin{smallmatrix}n\text{-}CH_2CH_2CH_3\\H\end{smallmatrix}$ | 500 | 100 |
| $n\text{-}C_{12}H_{25}SOCH=CHCON\begin{smallmatrix}n\text{-}CH_2CH_2CH_3\\H\end{smallmatrix}$ | 500 | 98 |
| $n\text{-}C_{14}H_{29}SCH=CHCON\begin{smallmatrix}C_2H_5\\C_2H_5\end{smallmatrix}$ | 500 | 89 |
| $n\text{-}C_{16}H_{33}SCH=CHCONH_2$ | 500 | 91 |
| $n\text{-}C_{16}H_{33}SOCH=CHCON\begin{smallmatrix}(C_3H_7O)_nH\\(C_3H_7O)_{n'}H\end{smallmatrix}$  (n+n')=15 | 500 | 88 |

The sulfenyl and sulfonyl compounds having the formula $R^1SO_n$—CH=CH—COX, wherein $R^1$ and X are the same as in formula (1) and n is one or 2, are described in Japanese Patent Applications Ser. No. 84707/75, filed July 10, 1975, and Ser. No. 84946/75, filed July 11, 1975, corresponding to U.S. Ser. No. 702,405, filed July 6, 1976, the entire contents of which are incorporated herein by reference.

The compounds of the invention, and the sulfinyl and sulfonyl derivatives thereof, possess antimicrobial activity against one or more of bacteria, fungi and yeasts. They can be used as preservatives and antiseptics in cosmetic oils, lotions and creams, and pharmaceutical oil, lotion and cream compositions for topical application. They can be used in place of the preservatives and antiseptics conventionally used in such compositions, at approximately the same concentration levels. In particular, they can be used in place of sodium salicylate, ethyl paraben, potassium sorbate and anhydrous sodium acetate, which are conventional preservatives, in prior art compositions that employ those conventional preservatives.

The embodiments of the invention in which an exclusive property or privilege is claimed are defined as follows:

1. A compound having the formula

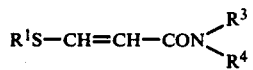

wherein $R^1$ is alkyl having 6 to 20 carbon atoms; and wherein $R^3$ and $R^4$, which can be the same or different, are hydrogen, unsubstituted alkyl having 1 to 6 carbon atoms or hydroxy-substituted alkyl having 2 to 6 carbon atoms.

2. A compound according to claim 1, wherein $R^1$ is alkyl having at least 8 carbon atoms.

3. A compound according to claim 2, wherein $R^1$ is straight chain alkyl.

4. A compound according to claim 2 in which

is —NH$_2$.

5. A compound according to claim 2 in which

is —N(CH$_3$)$_2$.

6. A compound according to claim 2 in which is —N(C₂H₅)₂.

7. A compound according to claim 2 in which

is —NH(CH₂CH₂CH₃).

8. A compound according to claim 2 in which

is —N(CH₂CH₂OH)₂.

9. A compound according to claim 1, having the formula n—C₁₆H₃₃SCH=CHCONH₂.

10. A compound according to claim 1, having the formula n—C₁₄H₂₉SCH=CHCON(C₂H₅)₂.

11. A compound according to claim 1, having the formula

12. A compound according to claim 1, having the formula n—C₁₂H₂₅SCH=CHCONH₂.

13. A compound according to claim 1, having the formula n—C₁₀H₂₁SCH=CHCON(CH₃)₂.

14. A compound according to claim 1, having the formula

15. A compound according to claim 1, having the formula n—C₁₂H₂₅SCH=CHCON(CH₃)₂.

16. A compound according to claim 1, having the formula n—C₈H₁₇SCH=CHCON(CH₃)₂.

17. A compound according to claim 1, having the formula n—C₈H₁₇SCH=CHCONH₂.

18. A compound according to claim 1 wherein R¹ is alkyl having 8 to 12 carbon atoms.

* * * * *